US 7,364,884 B2

(12) United States Patent
Hauer et al.

(10) Patent No.: US 7,364,884 B2
(45) Date of Patent: Apr. 29, 2008

(54) METHOD FOR PRODUCING A HYDROXYLATION CATALYST AND THE USE THEREOF

(75) Inventors: Bernhard Hauer, Fußgönheim (DE); Tilo Habicher, Speyer (DE); Rolf Schmid, Stuttgart (DE); Steffen Christian Maurer, Schwäbisch Gmünd (DE); Vlada Beniaminovna Urlacher, Stuttgart (DE); Holger Schulze, Schorndorf (DE); Norbert Huber, Basel (CH); Till T. Bachmann, Stuttgart (DE)

(73) Assignee: BASF Aktiengesellschaft (DE)

( * ) Notice: Subject to any disclaimer, the term of this patent is extended or adjusted under 35 U.S.C. 154(b) by 254 days.

(21) Appl. No.: 10/555,719

(22) PCT Filed: May 5, 2004

(86) PCT No.: PCT/EP2004/004748

§ 371 (c)(1),
(2), (4) Date: Nov. 7, 2005

(87) PCT Pub. No.: WO2004/099398

PCT Pub. Date: Nov. 18, 2004

(65) Prior Publication Data

US 2006/0216802 A1     Sep. 28, 2006

(30) Foreign Application Priority Data

May 9, 2003   (DE)   ................... 103 21 082

(51) Int. Cl.
*C12N 9/02* (2006.01)
*C12N 11/18* (2006.01)
*C12P 7/26* (2006.01)
*C12P 7/62* (2006.01)

(52) U.S. Cl. ............ 435/135; 435/146; 435/148; 435/155; 435/156; 435/157; 435/175; 435/177; 435/189

(58) Field of Classification Search .............. 435/135, 435/146, 148, 155, 156, 157, 175, 177, 189
See application file for complete search history.

(56) References Cited

U.S. PATENT DOCUMENTS 6,395,299 B1 *   5/2002   Babich et al. ............... 424/484
6,432,685 B1 *   8/2002   Hauer et al. ................ 435/157
7,052,913 B2 *   5/2006   Babich et al. ............... 435/484

OTHER PUBLICATIONS

Schwaneberg, U. et al., "A Continuous Spectrophotometric Assay for P450 BM-3, a Fatty Acid Hydroxylating Enzyme, and Its Mutant F87A", Analytical Biochemistry 269 (1999), pp. 359-366.

Ost, T. W. B. et al., "Rational Re-design of the Substrate Binding Site of Flavocytochrome P450 BM3", FEBS Letters 486 (2000), pp. 173-177.

Miles, C. S. et al., "Protein Engineering of Cytochromes P-450", Biochimica et Biophysica Acta 1543 (2000), pp. 383-407.

Maurer, S. C. et al., "Immobilisation of P450 BM-3 and an NADP Cofactor Recycling System: Towards a Technical Application of Heme-Containing Monooxygenases in Fine Chemical Synthesis", Adv. Synth. Catal. 345 (2000), pp. 802-810.

Wen, L-P. et al., "Cloning of the Gene Encoding a Catalytically Self-sufficient Cytochrome P-450 Fatty Acid Monooxygenase Induced by Barbiturates in Bacillus megaterium and Its Functional Expression and Regulation in Heterologous (Escherichia coli) and Homologous (Bacillus megaterium) Hosts", The Journal of Biological Chemistry 262(14) (1987), pp. 6676-6682.

Fulco, A. J. et al., "Occurrence of a Barbiturate-Inducible Catalytically Self-Sufficient 119,000 Dalton Cytochrome P-450 Monooxygenase in Bacilli", Life Sciences 40 (1987), pp. 1769-1775.

Iwuoha, E. I. et al., "Reactivities of Organic Phase Biosensors 3: Electrochemical Study of Cytochrome $P450_{cam}$ Immobilized in a Methyltriethoxysilane Sol-Gel", Electroanalysis 12(12) (2000), pp. 980-986.

Li, Q-S. et al., "Rational Evolution of a Medium Chain-Specific Cytochrome *P-450* BM-3 Variant", Biochimica et Biophysica Acta 1545 (2001), pp. 114-121.

Li, Q-S. et al., "Engineering Cytochrome P450 BM-3 for Oxidation of Polycyclic Aromatic Hydrocarbons", Applied and Environmental Microbiology 67(12) (2001), pp. 5735-5739.

Appel, D. et al., "A P450 BM-3 Mutant Hydroxylates Alkanes, Cycloalkanes, Arenes and Heteroarenes", Journal of Biotechnology 88 (2001), pp. 167-171.

Gill, I., "Bio-doped Nanocomposite Polymers: Sol-Gel Bioencapsulates", Chem. Mater. 13 (2001), pp. 3404-3421.

Farinas, E. T. et al., "Directed Evolution of a Cytochrome P450 Monooxygenase for Alkane Oxidation", Adv. Synth. Catal. 343 (2001), pp. 601-607.

Urlacher, V. B. et al., "Microbial P450 Enzymes in Biotechnology", Appl. Microbiol. Biotechnol. 64 (2004), pp. 317-325.

Seelbach, K. et al., "A Novel, Efficient Regenerating Method of NADPH Using a New Formate Dehydrogenase", Tetrahedron Letters, 37(9) (1996), pp. 1377-1380.

Tishkov, V. I. et al., "Pilot Scale Production and Isolation of Recombinant $NAD^+$ and $NADP^+$ —Specific Formate Dehydrogenases", Biotechnol. Bioeng. 64 (1999), pp. 187-193.

(Continued)

*Primary Examiner*—Herbert J. Lilling
(74) *Attorney, Agent, or Firm*—Connolly Bove Lodge & Hutz, LLP

(57) ABSTRACT

A process for preparing a hydroxylation catalyst by
  i) embedding a cystochrome P450 monooxygenase in a sol-gel matrix,
  ii) embedding an enzymatic NADPH-regenerating system in a sol-gel matrix,
and combining the two components i) and ii) unless they were already mixed together before the embedding.

6 Claims, No Drawings

OTHER PUBLICATIONS

Urlacher, V. et al., "Biotransformations Using Prokaryotic P450 Monoxygenases", Curr. Opin. Biotechnol. 13 (2002), pp. 557-564.

Li, Q-S. et al., "Directed Evolution of the Fatty-Acid Hydroxylase P450 BM-3 into an Indole-Hydroxylating Catalyst", Chem. Eur. J. 6(9) (2000), pp. 1531-1536.

Li, Q-S. et al, "Residue Size at Position 87 of Cytochrome P450 BM-3 Determines Its Stereoselectivity in Propylbenzene and 3-chlorostyrene Oxidation", FEBS Letters 508 (2001), pp. 249-252.

* cited by examiner

METHOD FOR PRODUCING A HYDROXYLATION CATALYST AND THE USE THEREOF

RELATED APPLICATIONS

This application is a national stage application (under 35 U.S.C. 371) PCT/EP2004/004748 filed May 5, 2004 which claims benefit to German application 103 21 082.2 filed May 9, 2003.

The present invention relates to a process for preparing a hydroxylation catalyst based on a cytochrome organic substrates using these hydroxylation catalysts.

Cytochrome P450 monooxygenases (called CYP hereinafter) catalyze the hydroxylation of a number of hydrophobic substrates at activated and nonactivated carbon atoms. This involves one oxygen atom of $O_2$ being incorporated into the substrate, while the other oxygen atom is reduced to $H_2O$ with simultaneous oxidation of nicotine adenine dinucleotide (phosphate) (NAD(P)H). This hydroxylation proceeds regio- and stereospecifically in many cases.

A particularly promising cytochrome P450 monooxygenase is the gene originally cloned from *Bacillus megaterium*, called CYP BM-3 hereinafter. This is a natural fusion protein with a size of 119 kDa and composed of a heme-comprising monooxygenase domain and an FAD- and FMN-comprising reductase domain (L. P. Wen, A. J. Fulco, J. Biol. Chem. 1987, 262, 6676-6682; A. J. Fulco, R. T. Ruettinger, Life Sci. 1987, 40, 1769-1775).

The natural substrates for CYP BM-3 are long-chain fatty acids (C12-C20), which are hydroxylated exclusively at the subterminal positions ω-1, ω-2, ω-3, in some cases with high enantioselectivity. Variants of CYP BM-3 (called muteins) also show activity toward unnatural substrates such as short-chain fatty acids (Ost et al. FEBS Lett. 2000, 486, 173-177; Li et al. Biochim. Biophys. Acta 2001, 1545, 114-121), indoles (Li et al. Chemistry 2000, 6, 1531-1536), polycyclic aromatic hydrocarbons (Li et al. Appl. Environ. Microbiol. 2001, 67, 5735-5739), alkanes (Appel et al. J. Biotechnol. 2001, 88, 167-171) and styrenes (Li et al. FEBS Lett. 2001, 508, 249-252).

Use of this CYP on the industrial scale is still impeded by the problems of low stability and product removal. A further disadvantage is the dependence of CYP on costly cofactors such as NADPH.

These problems can be solved in part by employing immobilized CYP for the hydroxylation reactions. However, many immobilization processes at least partly inactivate the enzyme, or the diffusion-controlled supply of necessary cofactors and substrates to the enzyme is limited.

It is an object of the present invention to provide a process which permits CYP to be immobilized with high enzymatic activity.

The invention relates to a process for preparing a hydroxylation catalyst by
  i) embedding a cytochrome P450 monooxygenase in a sol-gel matrix,
  ii) embedding an enzymatic NADPH-regenerating system in a sol-gel matrix,
     and combining the two components i) and ii) unless they were already mixed together before the embedding.

Cytochrome P450 monooxygenases (CYP) and their use in biotransformations are known to the skilled worker for example from E. T. Farinas et al. Adv. Synth. Catal. 2001, 343, 601-606 or V. Urlacher and R. D. Schmid Curr. Opin. Biotechnol. 2002, 13, 557-564.

CYP which are particularly well suited for the process of the invention are those originally isolated from microorganisms, especially those of the genus *Bacillus*.

A particularly suitable cytochrome P450 monooxygenase is the protein originally cloned from *Bacillus megaterium*, called CYP BM-3 hereinafter. This is a natural fusion protein with a size of 119 kDa and composed of a heme-comprising monooxygenase domain and an FAD- and FMN-comprising reductase domain (L. P. Wen, A. J. Fulco, J. Biol. Chem. 1987, 262, 6676-6682; A. J. Fulco, R. T. Ruettinger, Life Sci. 1987, 40, 1769-1775).

It is possible starting from this CYP BM-3 to produce by recombinant DNA techniques muteins which have modifications at particular amino acid positions compared with the wild-type CYP BM-3.

Muteins which are particularly suitable for the process of the invention are those having an amino acid other than Ala at position 74, and/or having an amino acid other than Phe at position 87, and/or having an amino acid other than Leu at position 188, and/or having an amino acid other than Phe at position 386. The modifications at the stated positions can be introduced either as single mutations or else cumulatively as multiple mutations.

Such a mutein, which is particularly suitable because of its wide substrate range, is the one having the following three amino acid substitutions compared with the wild-type CYP BM-3: position 74 Ala replaced by Gly, position 87 Phe replaced by Val, position 188 Leu replaced by Gln. This mutein can be employed in particular for the hydroxylation of alkanes and aromatic compounds.

A further mutein which is particularly suitable for the hydroxylation of β-ionone is the one having the following three amino acid substitutions compared with the wild-type CYP BM-3: position 74 Ala replaced by Glu, position 87 Phe replaced by Val, position 386 Phe replaced by Ser.

The embedding of enzymes in sol-gel matrices is described in a review article by I. Gill, Chem. Mater. 2001, 13, 3404-3421.

Particularly suitable sol-gel matrices for the process of the invention are those based on silica. Particularly suitable sol-gel matrices can be prepared from alkoxysilanes, especially from tetraalkoxysilanes, in particular tetraethoxysilane (TEOS) and tetramethoxysilane (TMOS). Concerning the preparation of the sol-gel matrices and the embedding of CYP, reference is made to the abovementioned article by Gill (I. Gill, Chem. Mater. 2001, 13, 3404-3421), which is incorporated herein by reference.

The enzymatic NADPH-regenerating system (called NADPH-RS hereinafter) consists of an $NAD^+$- or $NADP^+$-dependent enzyme which oxidizes a substrate to a product with simultaneous reduction of the $NAD^+$ to NADH or of the $NADP^+$ to NADPH. Suitable in particular for this purpose are all $NAD^+$- or $NADP^+$-dependent dehydrogenases, especially microbial dehydrogenases and especially formate dehydrogenases.

A preferred embodiment of the NADPH-RS is the $NADP^+$-dependent formate dehydrogenase (EC 1.2.1.2), abbreviated to FDH hereinafter, from *Pseudomonas* sp. 101. FDH catalyzes the $NAD^+$ dependent oxidation of formate to $CO_2$. The advantages of this system are the low substrate costs (formate) and the ease of removal of the resulting product ($CO_2$). A mutated form of FDH has a high activity with $NADP^+$ and can therefore be employed particularly well as NADPH-regenerating enzyme in combination with CYP. This particularly suitable mutated form of FDH is described by Tishkov et al. Biotechnol. Bioeng. 1999, 64, 187-193 and by Seelbach et al. Tetrahedron Lett. 1996, 37, 1377-1380. These specified documents describe both the natural and the mutated FDH, and processes for the preparation thereof, especially recombinant expression thereof in *E. coli*.

The embedding of CYP and NADPH-RS in a sol-gel matrix can take place simultaneously or in separate mixtures. Simultaneous embedding means that firstly a preparation of CYP, preferably a solution of CYP, is combined with a preparation of NADPH-RS, preferably a solution of NADPH-RS, and this combined preparation is then embedded in the sol-gel matrix.

Separate embedding means that a preparation of CYP, preferably a solution of CYP, is embedded in a sol-gel matrix and, in a second mixture, a preparation of NADPH-RS, preferably a solution of NADPH-RS, is embedded in a sol-gel matrix, and then these two mixtures are combined.

Separate embedding is preferably used for the process of the invention because subsequent flexible adjustment of the stoichiometric ratio of CYP to NADPH-RS is also possible with it.

The invention further relates to preparations which comprise a CYP and an NADPH-RS embedded in a sol-gel matrix. Preparations of this type can be prepared by the process described above. These preparations have the advantage that it is possible therewith for hydroxylation catalysts to be prepared in stable form which can be readily stored, and to be provided for use for specific hydroxylation reactions.

The invention further relates to processes for the enzymatic hydroxylation of a substrate using one of the hydroxylation catalysts which can be prepared according to the invention. A large number of classes of organic compounds are suitable as substrate, in particular long-chain fatty acids (C12-C20) which are hydroxylated in particular at the subterminal positions ω-1, ω-2, ω-3, but also short-chain fatty acids (Ost et al. FEBS Lett. 2000, 486, 173-177; Li et al. Biochim. Biophys. Acta 2001, 1545, 114-121), indoles (Li et al. Chemistry 2000, 6, 1531-1536), polycyclic aromatic hydrocarbons (Li et al. Appl. Environ. Microbiol. 2001, 67, 5735-5739), alkanes (Appel et al. J. Biotechnol. 2001, 88, 167-171) and styrenes (Li et al. FEBS Lett. 2001, 508, 249-252).

Conversion of these substrates with the hydroxylation catalyst prepared according to the invention takes place under the conditions known to the skilled worker for enzymatic reactions. The reaction can be carried out in a wide temperature range between 0 and 70, preferably between 5 and 50 and particularly preferably between 10 and 40° C.

The substrate to be hydroxylated can be dissolved or suspended in an organic or aqueous solvent, and with liquid substrates it is possible in some circumstances to dispense entirely with the addition of solvents. A mixture of aqueous and organic solvents, especially DMSO/water, is preferred for the conversion. DMSO/water mixtures in which DMSO amounts to 1-10% v/v are particularly suitable.

The hydroxylation reaction can be carried out batchwise or continuously. In a preferred embodiment with FDH as NADPH-RS, the reaction is carried out continuously, with continuous feeding of formate ions, in addition to the substrate to be hydroxylated, into the reaction, and continuous removal of the hydroxylated product and of the resulting $CO_2$ from the reaction.

The invention is illustrated further by the following examples.

Activity and Stability of the Sol-Gel Immobilized CYP BM-3

The model reaction used was the hydroxylation of p-nitrophenoxydecanoic acid (10-pNCA) which permits easy photometric detection of the p-nitrophenolate product formed (Schwaneberg et al. Anal. Biochem. 1999, 269, 359-366).

The immobilized enzyme forms a cloudy mixture after addition to the reaction mixture. Direct kinetic experiments to determine the activity of the sol-gel-embedded CYP BM-3 were therefore impossible. The activity of the sol-gel-embedded CYP BM-3 was therefore determined by incubating all the components of the standard pNCA test for a certain time and then centrifuging in order to remove the yellow reaction product from the solid catalyst. The absorption at 410 nm was then determined from the supernatant.

Investigations of the long-term stability revealed that the CYP BM-3 embedded in the sol-gel suffered no loss of activity over 36 days at 4° C. The free enzyme had a half-life of 26 days on storage in 50 mM KPi and a half-life of 288 days on stabilization with 50% glycerol. The half-life of the sol-gel-embedded enzyme is considerably longer than these 288 days.

The immobilized enzyme of the invention displays remarkably high stability even at 25° C. The half-life at this temperature is determined to be 29 days.

A further selective hydroxylation reaction was carried out with the sol-gel-embedded CYP BM-3 on the substrate n-octane. 79% of the precursor were hydroxylated. The regio isomers 2-octanol, 3-octanol and 4-octanol were obtained in a molar ratio of 1:2.1:1.6 (detected by gas chromatography).

A further selective hydroxylation reaction was carried out with the sol-gel-embedded CYP BM-3 on the substrate naphthalene. 77% of the precursor were hydroxylated. The main product obtained was 1-naphthol (85%), and 2-naphthol was obtained as by-product (15%) (detected by gas chromatography).

Cofactor Regeneration

Two possibilities were investigated for the cofactor regeneration according to the invention. Co-immobilization of both enzymes (CYP and FDH) was investigated in a first series of experiments, and the two enzymes were immobilized separately and then mixed in the ratio 1:1 (m/m) in a second series of experiments. In both cases, the embedding took place in a TEOS sol-gel matrix.

Co-immobilized enzymes from the first experimental series were put into the p-NCA test with a 10-fold excess of p-NCA over oxidized $NADP^+$.

The activity of the separately immobilized FDH in combination with separately immobilized CYP was considerably higher than with the co-immobilized enzymes.

After a reaction time of three hours, the co-immobilized enzymes showed a conversion of up to 28% of the pNCA, while the mixture of separately immobilized enzymes led to a conversion of up to 75%.

These results make it possible to operate a continuously operating bioreactor based on a sol-gel-embedded CYP with NADPH-RS.

We claim:

1. A process for preparing a hydroxylation catalyst by
   i) embedding a cytochrome P450 monooxygenase in a sol-gel matrix, ii) embedding an enzymatic NADPH-regenerating system in a sol-gel matrix, and combining the two components i) and ii), or embedding a mixture of a cytochrome P450 monooxygenase and an enzymatic NADPH-regenerating system in a sol-gel matrix.

2. The process as claimed in claim 1, wherein enzymes which had originally been isolated from the genus *Bacillus* are used as monooxygenases.

3. The process as claimed in claim 2, wherein the monooxygenases have been isolated from *Bacillus megaterium*.

4. A preparation comprising a cytochrome P450 monooxygenase and an enzymatic NADPH-regenerating system in a sol-gel matrix.

5. A process for the enzymatic hydroxylation of a substrate by reacting the substrate with a hydroxylation catalyst which can be prepared by the process as claimed in claim 1.

6. The process as claimed in claim 5, wherein β-ionone is employed as substrate.

* * * * *